US 6,685,017 B2

(12) United States Patent
Erickson

(10) Patent No.: US 6,685,017 B2
(45) Date of Patent: Feb. 3, 2004

(54) CONTAINER FOR TRANSPORTATION AND DISPENSING OF UNUSED SYRINGES AND FOR STORAGE OF USED SYRINGES

(75) Inventor: Charles W. Erickson, Minneapolis, MN (US)

(73) Assignee: Ulti Med, Inc., St. Paul, MN (US)

( * ) Notice: Subject to any disclaimer, the term of this patent is extended or adjusted under 35 U.S.C. 154(b) by 3 days.

(21) Appl. No.: 10/047,074

(22) Filed: Jan. 14, 2002

(65) Prior Publication Data
US 2003/0132129 A1 Jul. 17, 2003

(51) Int. Cl.[7] .......................... B65D 83/02; B65D 85/20
(52) U.S. Cl. ...................... 206/366; 206/370; 206/817; 221/101
(58) Field of Search ................ 206/366, 370, 206/494, 570–572, 817; 221/26, 34, 66, 97, 98, 100, 102, 101

(56) References Cited

U.S. PATENT DOCUMENTS 3,221,928 A * 12/1965 Horn ........................... 221/34
5,152,394 A * 10/1992 Hughes ....................... 206/366
5,190,185 A * 3/1993 Blechl ............................ 221/1
5,494,158 A 2/1996 Erickson
5,740,909 A * 4/1998 Nazare et al. ............... 206/366

* cited by examiner

Primary Examiner—Jim Foster
(74) Attorney, Agent, or Firm—Roger W. Jensen

(57) ABSTRACT

A multifunctional box for facilitating the safe transport of the box and a plurality of unused syringes therein. The box further facilitates the safe sequential dispensing of unused syringes from the box, with concurrent facilitation of the safe sequential feeding of used syringes into the box for safe storage therein. The box includes a container having an open top and an exit opening near the bottom sized to permit sequential withdrawal therethrough of either unused syringes and/or packets of syringes. A dividing tray is provided within the container which is used to collect used syringes while simultaneously to provide a blockage between the used syringes and the exit opening. A cover is attached to open top of the container and supports a used syringe feed means which has a first preselected position for receiving a used syringe, which then is moveable to a second preselected position for feeding used syringes into the tray for safe storage.

16 Claims, 5 Drawing Sheets

CONTAINER FOR TRANSPORTATION AND DISPENSING OF UNUSED SYRINGES AND FOR STORAGE OF USED SYRINGES

BACKGROUND OF THE INVENTION

1. Field of the Invention

This invention relates to syringes which have a variety of uses, a very common one being the use of the syringe to inject a preselected medication into a human. Syringes are used both in a professional setting such as at a hospital, clinic, or offices of doctors or other medical professionals, and also by individual users, e.g., a diabetic requiring frequent injections of insulin, this latter use being typically at the individual user's place of residence.

2. Description of the Prior Art

The safe storage of syringes is extremely important; this is especially the case for a "used" syringe which may, after the needle thereof is removed from the tissue into which it had penetrated, be contaminated with a possible deadly bacteria or virus. For a number of years, partly because of an awareness of the possible transmittal of diseases such as hepatitis and AIDS, various boxes and other containers have been developed and provided for the professional settings safe storage of used syringes. Such containers are sometimes referred to as "sharps-boxes". A typical sharps-box would be a container securely attached to the wall within the professional setting, with a locked cover or the like, and with an opening permitting sequential insertion of used syringes into the box. From time to time, trained staff empty the used syringes into, hopefully, a safe disposal means for handling medical waste.

Individual users, on the other hand, have not typically had such "safe" storage arrangements. A more typical arrangement for an individual user would be to insert a used syringe into the mouth of an empty one-gallon plastic jug which, in practice, could hold a significant number of used syringes before it got full or otherwise required disposal. There are obvious risks associated with this type of storage. The user could inadvertently tip over the jug or otherwise cause one or more used syringes to come out of the container and into potential contact with the user and/or other people in that vicinity. Alternately, the user might put the filled or partly filled jug into the trash disposal system, which would create potential risk to others in society.

The individual user of syringes typically purchases syringes at a retail outlet such as a drug store, or other retailing establishment. Syringes are frequently vended in flat-like packets containing a preselected number of syringes, e.g., ten; sometimes the syringes are vended individually in single or, more typically, in bulk quantities. The user transports the unused syringes to his or her place of residence.

SUMMARY OF THE INVENTION

The present invention provides a multifunctional box for facilitating (i) the safe transport of the box and a plurality of unused syringes therein to a syringe user, (ii) the safe sequential dispensing of said unused syringes from said box, and (iii) the safe sequential feeding of used syringes into the box for safe storage therein. A typical usage of the invention would be for an individual to purchase the box (filled with unused syringes, either individual or in packets) at a vending establishment, to transport the box to his or her place of residence where the unused syringes would be withdrawn from the box as needed and the used syringes would be sequentially fed or inserted back into the box but, importantly, the used syringes would be hygienically separated from the unused syringes remaining in the box.

More specifically, the invention provides a multifunctional box comprising a container having an open top, a bottom, and a plurality of sides integral therewith defining a preselected volume for storing a preselected number of unused syringes. The syringes may be individualized or may be in packets containing a preselected number, e.g., ten. The container additionally has an exit opening adjacent to the bottom thereof, the opening being sized to permit sequential withdrawal therethrough of unused syringes.

The invention further provides a dividing tray having a bottom and a plurality of sides so as to provide a form of subcontainer. The tray is sized to fit in close but unrestricted relationship the sides of the main container. The tray is adapted to be rested upon and supported by either unused syringes positioned below, or by the bottom of the container. That is, the tray is adapted to be supported with the bottom thereof on top of a plurality of unused syringes in the container. Because the tray is not restricted from movement within the container, as unused syringes are withdrawn from the container through the aforesaid exit opening, the tray moves under the influence of gravity vertically downward towards the bottom of the container. The clearance between the sides of the container and the tray are selected to preclude the passage therebetween of a used syringe.

The invention additionally provides a cover adapted to be attached to and locked to the open top of the container. Additionally, a used syringe feed means or mechanism is positioned within and supported by the cover, and has at least one used syringe receiving means having a first preselected position for receiving a used syringe, and then being moveable, e.g., rotated to a second preselected position for feeding used syringes into the tray for safe storage therein.

BRIEF DESCRIPTION OF THE DRAWINGS

FIG. 1A is a partial view of the container shown in FIG. 1, depicting an alternate usage, i.e., having individual unused syringes removed from the exit opening as contrasted with the FIG. 1 depiction of a packet of unused syringes being removed from the exit opening.

DETAILED DESCRIPTION OF THE INVENTION

Figure 1:
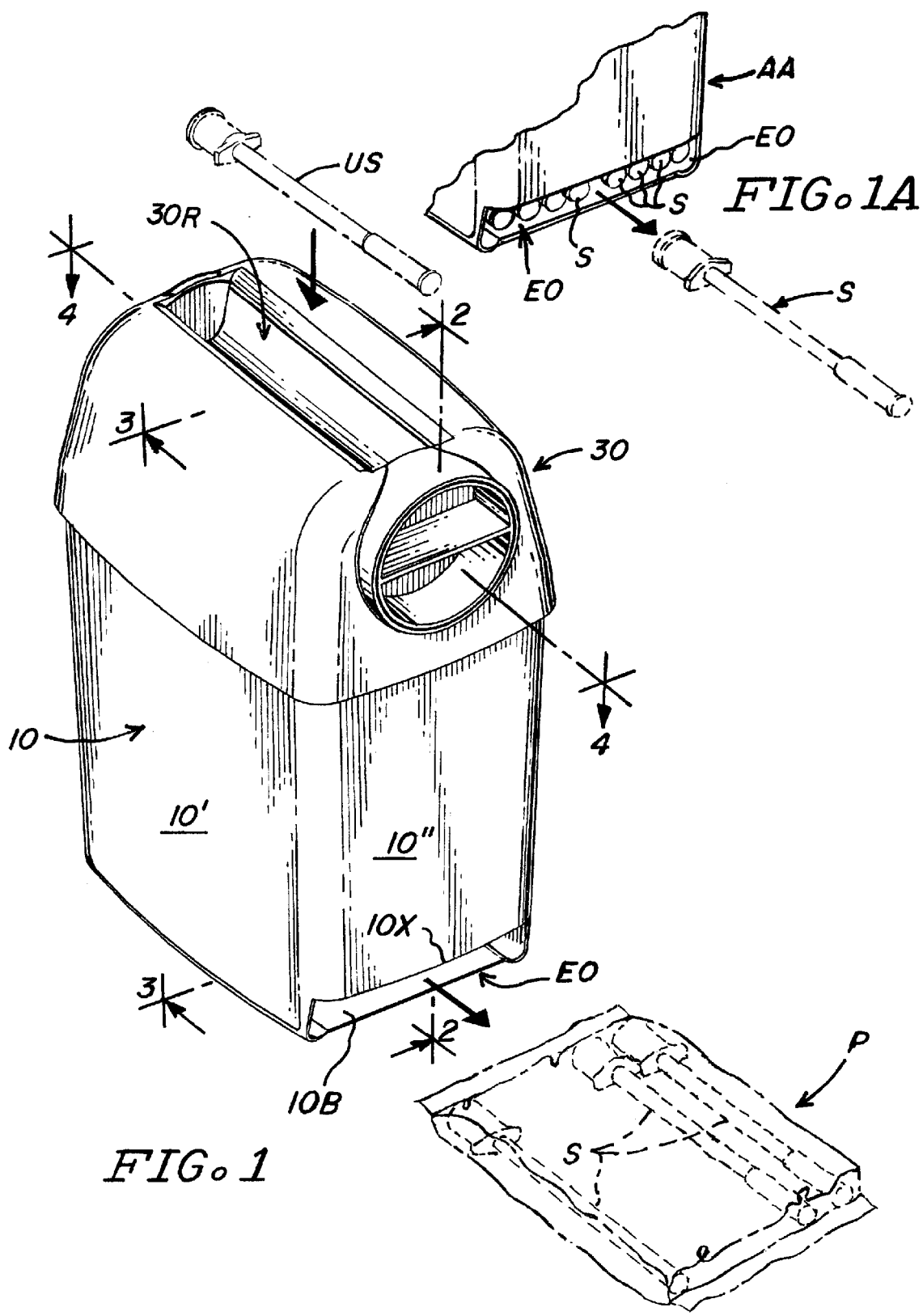
FIG. 1 is an isometric view of a first embodiment of my invention showing the top, a side, and an end thereof.
Figure 2:
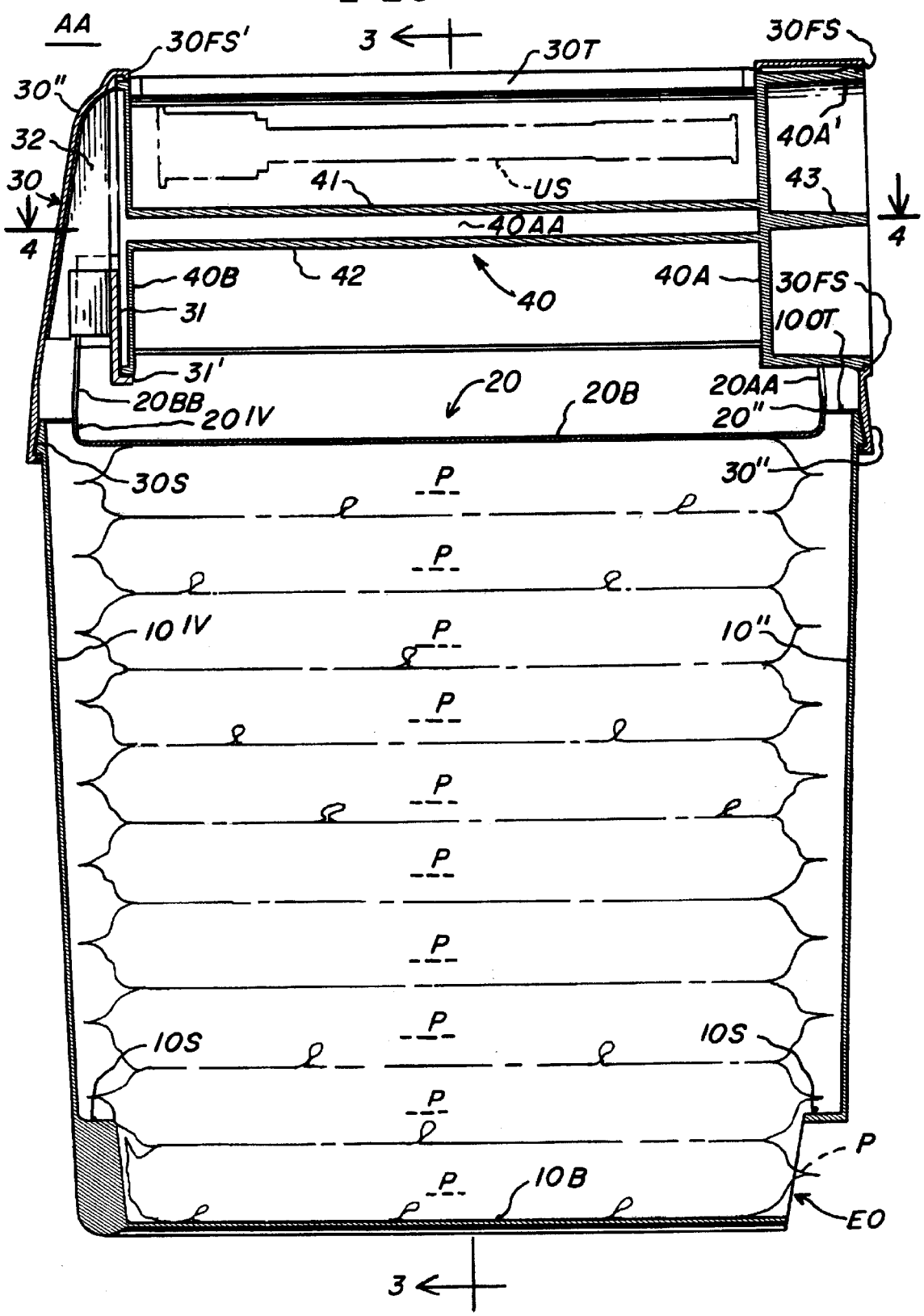
FIG. 2 is cross-sectional view of the apparatus shown in FIG. 1, as viewed along section lines 2—2 thereof and as viewed along section lines 2—2 of FIG. 3.
Figure 3:
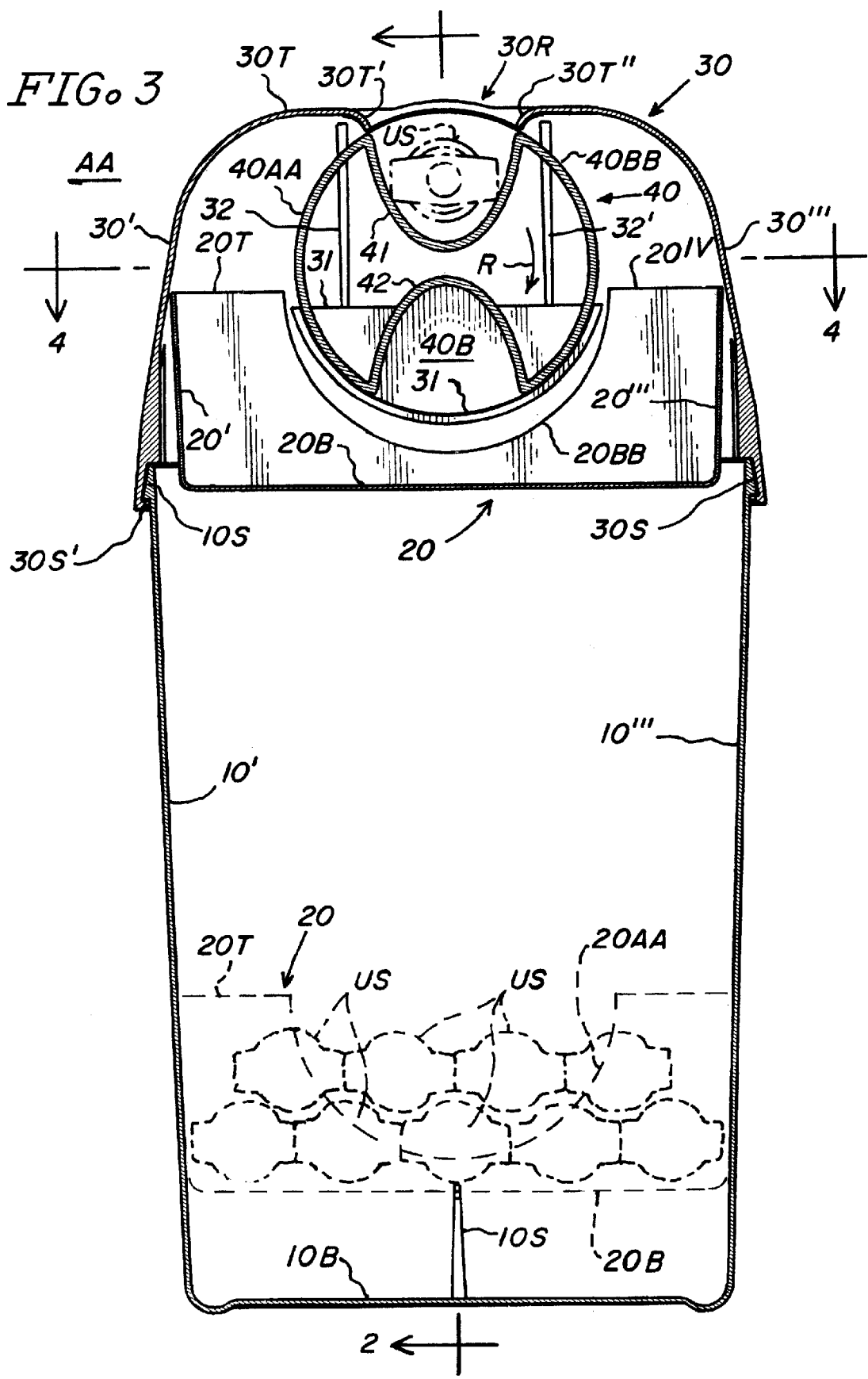
FIG. 3 is a cross-sectional view of the apparatus shown in FIG. 1, as viewed along section lines 3—3 thereof and as viewed along section lines 3—3 of FIG. 2.
Figure 4:
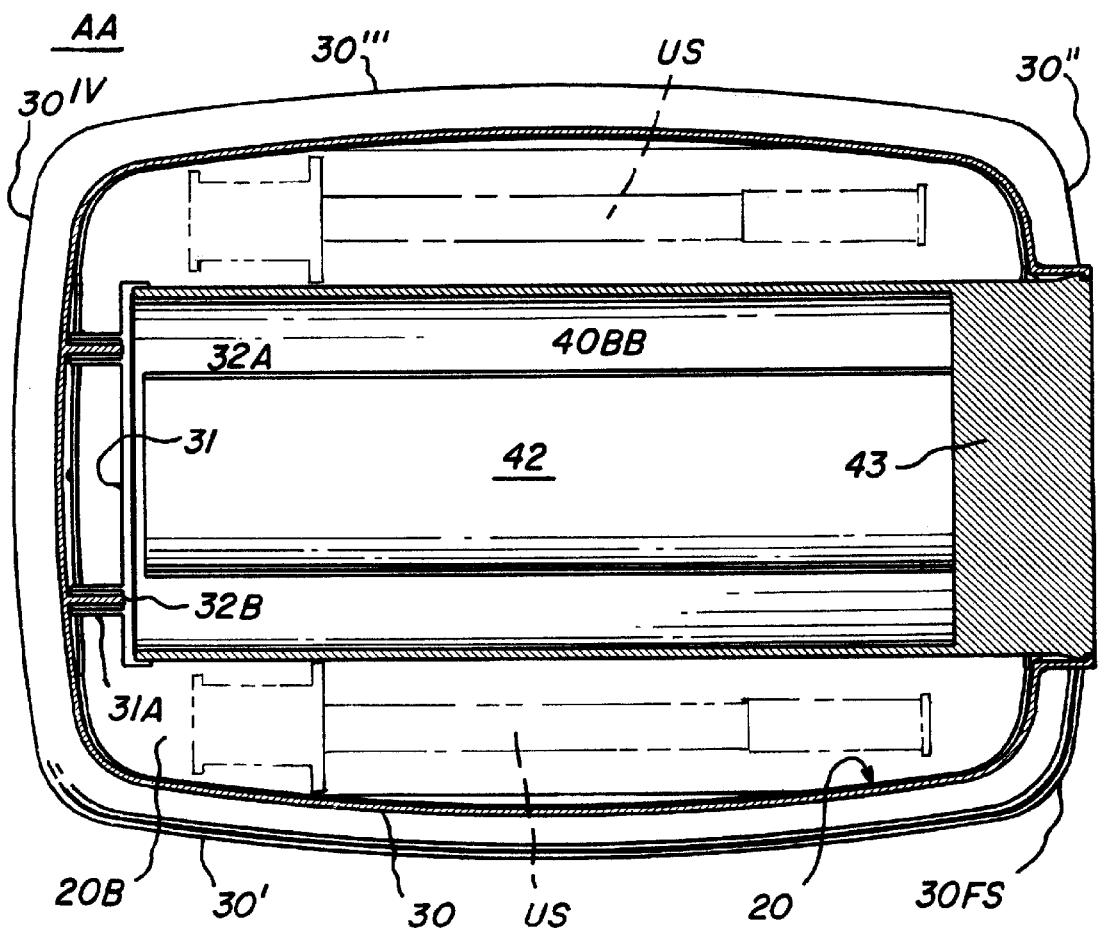
FIG. 4 is a cross-sectional view of the apparatus shown in FIG. 1, as viewed along section lines 4—4 thereof and as viewed along section lines 4—4 of FIG. 3.

Referring to FIG. 1, a multifunctional box AA comprises in part a container 10 shown in greater detail in FIGS. 2, 3, and 4. The container 10 has an open top 10OT, a bottom 10B, and a plurality of sides 10', 10", 10'", and 10IV. As shown, the sides 10' and 10'" are of greater width than the sides 10" and 10IV. The sides of the container are preselected so as to efficiently accommodate a plurality of unused syringes S, such as is depicted in FIG. 1A, or a plurality of packets of unused syringes P, such as is shown in FIG. 1. Thus, sides 10' and 10'" are sufficiently long so as to accommodate the longitudinal length of the syringe S, FIG. 1A showing a plurality of unused syringes S being arranged lying in close side-by-side parallel relationship. Further, the sides 10" and 10IV are sufficiently wide in the transverse sense so as to permit the storage of a plurality of packets P stacked at the point of manufacture in side-by-side stacked relationship as is shown in FIG. 2. As can be noted in FIGS. 1 and 2, side 10" of container 10 does not quite extend to the bottom 10B; it terminates at 10X to thus define an exit opening EO for the selective removal of packets P of syringes or individual unused syringes S by the user of box AA. Packets of syringes are typically sold by retail establishments to individual users, either as individual packets or in a larger container having a plurality of packets. The present invention contemplates that the individual user would purchase the entire container AA prefilled prior to purchase with either packets or individual unused syringes.

The multifunctional box of the invention includes a cup-like dividing tray 20, shown clearly in FIGS. 2 and 3, having a bottom 20B and a plurality of sides 20', 20", 20'" and 20IV, the bottom and sides being sized to fit in close but unrestricted relationship with the sides of the container 10. The tray's initial position is shown in FIGS. 2 and 3, up at the top of the container 10 and adapted to be resting upon either a plurality of stacked packets, or a plurality of unused syringes, depending upon which choice is made by the purchaser. As individual packets P or individual syringes S are withdrawn from the exit opening EO, the tray 20, under the influence of gravity, will move downwardly or towards the bottom 10B of the container, and also carrying used syringes therewith, as will be explained below. The tray has the potential to descend all the way, to be proximate to the bottom of the container 10 to a position depicted in phantom in FIG. 3, wherein the bottom 20B of the tray is abutted against abutments 20S and 20S' which are shoulders on the insides of sides 10IV and 10" of the container.

The sides 20' and 20'" extend from the bottom 20B to the top 20T of the tray 20 as is clearly shown in FIG. 3. The other sides, 20" and 20IV are provided with semicircular cutouts 20AA and 20BB respectively, as is shown in FIGS. 2 and 3. The cutouts 20AA and 20BB are provided so as to accommodate the used syringe feed means to be described below.

The multifunctional box AA further includes a cover 30 adapted to be attached to and locked to the open top 10OT of the container 10. More specifically, the cover 30 is shown as an inverted elongated cup having sides 30', 30", 30'" and 30IV sized to fit over and be attached to the open top 10OT of the container 10. The attaching and locking means is shown as an outwardly extending shoulder 10S at the outer periphery of the top of container 10, and tapered inwardly toward the top as is shown in FIGS. 2 and 3. A tapered inner surface 30S on the inside lower periphery of cover 30 is sized to complement the tapered surface 10S of the container. As indicated, the cover and the container are sized so as to fit snugly together and to be locked in place by a bottom latch 30S' which is integral with cover 30 so as to lock the cover to the container.

The top 30T of the cover has an opening 30R for receiving used syringes US, the opening being defined by parallel, spaced apart curved edges 30T' and 30T" as is clearly shown in FIG. 3, edge 30T' being shown in FIG. 2.

The cover 30 provides a moveable support, e.g., a rotatable support for a used syringe feed means to be described below. At the left end of cover 30 as shown in FIG. 2, such support comprises (i) semicircularly-shaped member 31 having a lip or shoulder 31' and attached to the inside of the cover by vertically extending ribs 32 and 32', and (ii) a curved surface 30 FS'. The support at the right end of cover 30 as shown in FIG. 2 is an almost complete circular shaped surface 30FS in cover 30, i.e., a circularly-shaped opening for journaling a cylindrically-shaped end 40A of used syringe feed means 40. The other end 40B of used syringe feed means 40 is supported for rotation by the shoulder or lips 31' of member 31.

The used syringe feed means 40 in general is an elongated barrel-shaped or generally-cylindrically-shaped member having two curved outer portions 40AA and 40BB as is clearly shown in FIG. 3; the member further having a pair of opposed used syringe receiving pockets 41 and 42 which respectively connect the outer curved sections 40AA and 40BB. Referring to FIG. 3, it is seen that pocket 41 is sized so as to receive a used syringe US via the opening 30R.

Referring to FIG. 3, the used syringe US shown in phantom within the pocket recess 41 of the feed means 40 may be put within the container for safe storage easily by manual rotation of the barrel 40 in the direction of the arrow R after approximately 180 degrees of rotation of the barrel about its rotational axis, the used syringe then will be free to fall under the influence of gravity into the cup-like top of tray 20 where it will be safely stored and prevented by the invention from ever being available for exit through the exit opening EO. It will be understood that, initially, the tray 20 will be generally positioned near the top of the container 10, on the assumption that container 10 will be substantially full of either unused individual syringes or packets of syringes. In any event, as unused syringes and packets are removed through the opening EO for use by the user, the tray, as indicated, will begin traveling downwardly under the influence of the weight of the tray per se and used syringes therein toward the bottom 10B of the container. FIG. 3 shows, in phantom, a plurality of used syringes US within the tray (also shown in phantom) with the tray being at its lowermost or bottommost position, resting on the shoulders 10S and 10S' of the container. It will be noted that when the tray 20 is in this position, it serves as a block between the used syringes and the exit opening EO. Thus, used syringes may not inadvertently or otherwise be removed from the container once they have been inserted into the container via the cover 30 and used syringe feed means 40.

As indicated, the clearance between the sides of tray 20 and container 10 prevents any passage therebetween of a syringe. Thus, the invention provides a safe storage of and dispensing of unused syringes; the safe storage is not compromised by used syringes being collected, as aforesaid, in cup-like tray 20.

It should be further understood that the feed means 40 does not permit, in normal usage thereof, any used syringe being somehow retransferred from within the container 10 out through the opening 30R. To completely rule out such an occurrence, the apparatus shown in FIGS. 5, 6, and 7 has been provided, which will now be described in detail.

Figure 5:
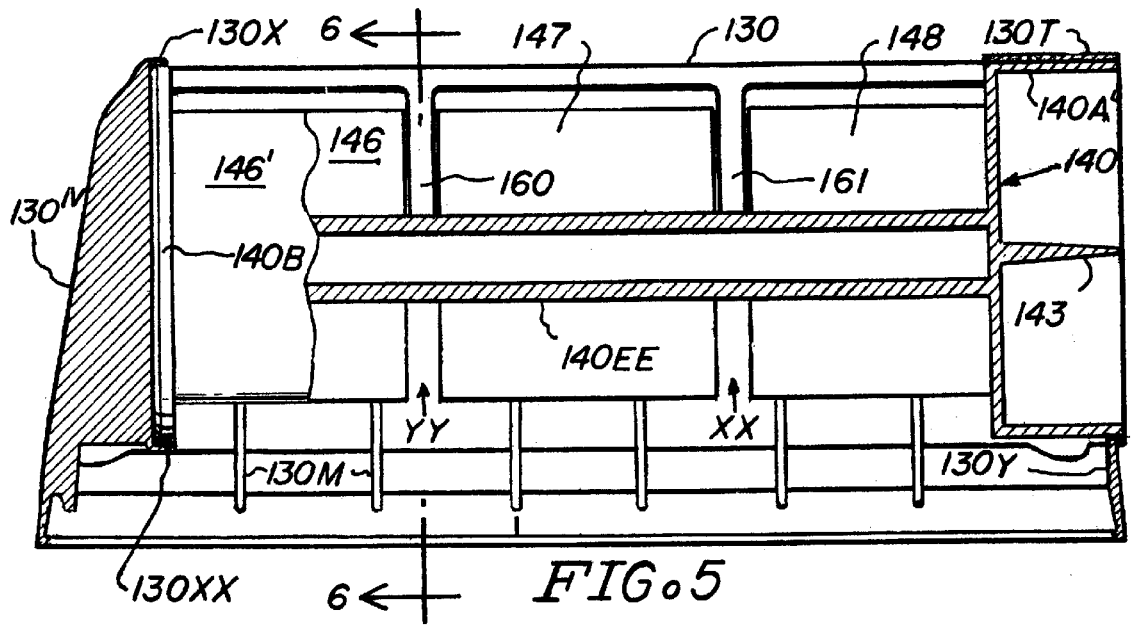
FIG. 5 is a view, partly in section, of a second embodiment of the cover as viewed along section lines 5—5 of FIG. 6.
Figure 6:
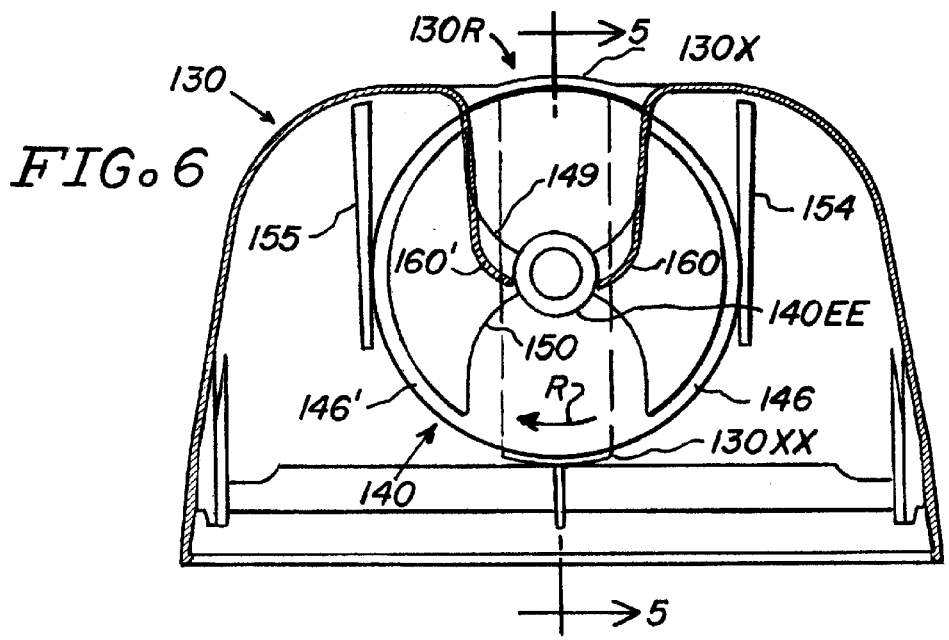
FIG. 6 is a cross-sectional view of the apparatus shown in FIG. 5, as viewed along section lines 6—6 thereof.
Figure 7:
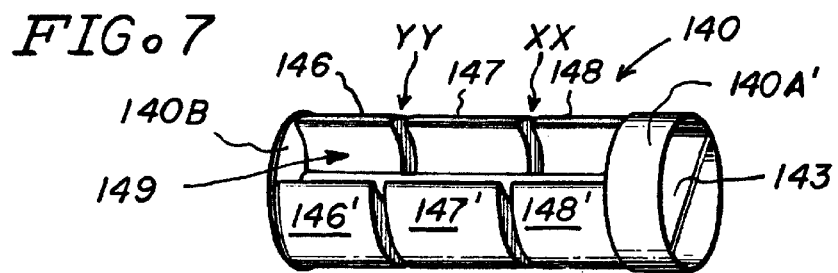
FIG. 7 is an isometric view of the used syringe feed means depicted in FIGS. 5 and 6.

A modified barrel 140 has a relatively small diameter central core 140EE to which are integrally connected two sets of semicircularly-shaped segments, the first set 146, 147, and 148 positioned on one side of the rotational axis, and a matching set 146', 147', and 148' positioned on the opposite side of the rotational axis, with the aforesaid sets defining therebetween used syringe receiving recesses 149 and 150, best shown in FIG. 6. The segments 146–148 and 146'–148' are spaced apart by slots YY and XX as is shown in FIGS. 5 and 7. Used syringe feed means 140 further includes at the right end as shown in FIG. 7 a cylindrically-shaped top 140A' having, within, a turning means 143. At the left end, as shown in FIG. 7, is a hub-member 140B which is adapted to be rotationally supported the lower bearing means 130XX shown in FIGS. 5 and 6, and at the top by a bearing means 130X as is shown in FIG. 5. The portion 140A' of the used syringe feed means 140 is supported for rotation by an appropriate bore 130Y provided in the cover 130.

A key feature of this modification or embodiment of the invention are a plurality of fingers 160, 161, and 160' and 161' which are integral with the cover 130 and which curve downwardly as is shown in FIG. 6, i.e., within the slots or spaces XX and YY of the barrel 140, the lower extremities of said fingers being in close proximity and/or in touching relationship with the central core 140EE. The fingers 160, 161, 160' and 161' are all spring-like, or resilient, so that they may be momentarily deflected sufficiently when the barrel 40 is rotated to permit the transfer of a used syringe from the receiving recess 149 (when the barrel is rotated) to be transferred to and/or deposited in the tray 20 within the container 10 positioned below the cover 130. Thus, the spring fingers will permit such a transfer from the outside of the cover through the opening 130R into the tray, as aforesaid, but the fingers will prevent any reverse transfer from within the container to the outside of the cover via opening 130R.

Additional features of the apparatus shown in FIGS. 5–7 include a pair of barrel side supports 154 and 155 shown in FIG. 6, which help stabilize the barrel. A plurality of ribs 130M are provided, as is shown in FIG. 5, for providing a certain level of reinforcement or strength to the cover 30.

While the preferred embodiment of the invention has been illustrated, it will be understood that variations may be made by those skilled in the art without departing from the inventive concept. Accordingly, the invention is to be limited only by the scope of the following claims.

I claim:

1. A multifunctional box for facilitating (i) the safe transport of said box and a plurality of unused syringes therein to a syringe user, (ii) the safe sequential dispensing of said unused syringes from said box, and (iii) the safe sequential feeding of used syringes into said box for safe storage therein, said box comprising:
    (a) a container having an open top, a bottom and a plurality of sides integral therewith defining a preselected volume for storing a preselected number of unused syringes, said container further having an exit opening adjacent to said bottom and sized to permit sequential withdrawal therethrough of said unused syringes;
    (b) a dividing tray having a bottom and a plurality of sides and sized to fit in close but unrestricted relationship with said sides of said container, said tray being adapted to be rested and supported with the bottom thereof on top of a plurality of unused syringes in said container and thence sequentially moving vertically downward toward said bottom of said container as unused syringes are removed from said bottom of said container through said exit opening;
    (c) a cover adapted to be attached to said open top of said container; and
    (d) a used syringe feed means positioned within and supported by said cover and having at least one used syringe receiving means, said used syringe receiving means having a first preselected position for receiving an used syringe and being movable to a second preselected position for feeding used syringes into said tray for safe storage therein.

2. The multifunctional box of claim 1 including an elongated opening in said cover and sized to permit passage therethrough of a used syringe.

3. The multifunctional box of claim 2 wherein said opening in said cover is adjacent to and in register with said used syringe receiving means when said used syringe receiving means is in said first preselected position.

4. The multifunctional box of claim 1 wherein said unused syringes are prepackaged in packets each containing a plurality of unused syringes and said exit opening is sized to facilitate the sequential withdrawal of said packets from said container.

5. The multifunctional box of claim 1 including locking means for locking together said cover and said container.

6. The multifunctional box of claim 1 wherein said used syringe feed means comprises a barrel-shaped rotatable member rotatably supported by said cover and having at least two angularly spaced apart and longitudinally extending syringe receiving recesses.

7. The box of claim 6 further characterized by including means for facilitating manual rotation of said barrel from a first angular position whereat a used syringe may be positioned in one of said at least two recesses to a second angular position whereat said used syringe is released for gravity transfer thereof into said tray for safe storage therein.

8. The box of claim 6 wherein said barrel has two of said recesses spaced apart approximately 180 degrees.

9. The box of claim 1 Wherein said container includes stop means adjacent said bottom of said container sized to limit the downward vertical travel of said dividing tray.

10. A multifunctional box for facilitating (i) the safe transport, within said box, of a plurality of flat-like, generally-rectangular-shaped packets, each having a preselected number of unused syringes, to a syringe user, (ii) the safe sequential dispensing of said packets from said box, one at a time, as selected by said user, and (iii) the safe sequential feeding of used syringes, one at a time, into said box for safe storage therein, said packets having preselected width, length and a thickness substantially less than said length or said width, said box comprising:
    a) a container having an open top, a bottom and a plurality of sides integral therewith defining a preselected volume for storing a preselected number of said packets arranged in a stack vertically in side by side relationship, said container having a packet exit opening in one of said sides adjacent to said bottom, said packet exit opening being sized to permit the sequential withdrawal therethrough of said packets;
    b) a dividing tray having a bottom and a plurality of sides and sized to fit in close but unrestricted relationship with said sides of said container, said tray being adapted to be rested with the bottom thereof on top of a stack of said packets in said container and thence sequentially moving vertically downward, relative to said sides of said container, as individual packets are removed from the bottom of said container through said packet exit opening;
    c) a cover adapted to be attached to said open top of said container; and d) a used syringe feed member rotatably supported on said cover and having at least one used syringe receiving recess open and accessible in one preselected position to receive an used syringe which, after said feed member is rotated to a second preselected position, is discharged into said dividing tray.

11. The box of claim 10 further characterized by said container having preselected vertical height, four sides, and a transverse rectangular cross section preselected to freely but snugly receive said stack of packets.

12. The box of claim 10 wherein said cover includes an elongated opening sized to permit the passage therethrough of a used syringe.

13. The box of claim 12 wherein said used syringe feed member is (i) elongated and has two ends respectively journaled in support means integral with said cover, and (ii) in register with said elongated opening of said cover so that a used syringe may be deposited through said opening into said used syringe receiving recess of said syringe feed member.

14. The box of claim 13 wherein said bottom and sides of said dividing tray are integrally connected to form a fluid-tight receptacle.

15. The box of claim 11 or 14 wherein said container includes stop means adjacent the bottom thereof to limit the downward vertical travel of said dividing tray.

16. The box of claim 10 wherein said cover is locked to said open top of said container.

* * * * *